United States Patent
Rosenquist

(10) Patent No.: US 9,790,011 B2
(45) Date of Patent: Oct. 17, 2017

(54) NON-REMOVABLE TAMPER RESISTANT LID

(71) Applicant: Carmel Pharma AB, Göteborg (SE)

(72) Inventor: Tobias Rosenquist, Kållered (SE)

(73) Assignee: Carmel Pharma AB, Gothenburg (SE)

( * ) Notice: Subject to any disclaimer, the term of this patent is extended or adjusted under 35 U.S.C. 154(b) by 0 days.

(21) Appl. No.: 14/883,026

(22) Filed: Oct. 14, 2015

(65) Prior Publication Data

US 2016/0031614 A1 Feb. 4, 2016

Related U.S. Application Data

(63) Continuation of application No. 14/119,200, filed as application No. PCT/EP2011/058960 on May 31, 2011, now Pat. No. 9,162,803.

(51) Int. Cl.
*B65D 47/02* (2006.01)
*B65D 55/02* (2006.01)
(Continued)

(52) U.S. Cl.
CPC ............ *B65D 55/02* (2013.01); *A61B 50/362* (2016.02); *B65B 7/2835* (2013.01); *B65D 41/04* (2013.01);
(Continued)

(58) Field of Classification Search
CPC .... B65D 41/00; B65D 41/04; B65D 41/0471; B65D 41/0478; B65D 41/62; B65D 43/14;
(Continued)

(56) References Cited

U.S. PATENT DOCUMENTS

| | | |
|---|---|---|
| 3,603,470 A | 9/1971 | Armour |
| 5,000,332 A | 3/1991 | Whitacre |
| (Continued) | | |

FOREIGN PATENT DOCUMENTS

| | | |
|---|---|---|
| DE | 3605963 | 8/1987 |
| EP | 0127943 A1 | 12/1984 |
| (Continued) | | |

OTHER PUBLICATIONS

Partial European Search Report in EP 16169092 dated Jul. 5, 2016, 5 pages.
PCT International Search Report in PCT/EP2011/058960, mailed Nov. 24, 2011, 3 pgs.

*Primary Examiner* — Steven A. Reynolds
*Assistant Examiner* — Javier A Pagan
(74) *Attorney, Agent, or Firm* — Servilla Whitney LLC

(57) ABSTRACT

The present invention relates to a tamper resistant lid for a container. The lid exhibits a center axis (X) and includes an outer and an inner member. The outer and inner members are further adapted to be substantially prevented from displacement along the center axis (X) with respect to each other. At least a part of the inner member includes threads enabling a threaded connection to the container by means of rotating the outer member in a first direction. The lid further includes at least one stop member preventing the inner member from rotation with respect to the outer member. The at least one stop member is adapted to be controllably disabled with a designated force after said inner member has been connected to the container, so that the outer member can be freely rotated with respect to the inner member to thereby prevent removal of the lid from the container. The present invention enables the sealing of a container, while substantially preventing the container from being reopened.

16 Claims, 3 Drawing Sheets

(51) Int. Cl.
*B65D 51/18* (2006.01)
*B65B 7/28* (2006.01)
*B65D 50/00* (2006.01)
*B65D 41/04* (2006.01)
*A61B 50/36* (2016.01)

(52) U.S. Cl.
CPC .............. *B65D 50/00* (2013.01); *B65D 51/18* (2013.01); *B65D 2251/009* (2013.01); *B65D 2251/0015* (2013.01); *B65D 2251/0028* (2013.01); *B65D 2251/0078* (2013.01); *B65D 2255/20* (2013.01)

(58) Field of Classification Search
CPC .... B65D 43/22; B65D 39/00; B65D 39/0052; B65D 39/0076; B65D 50/00; B65D 50/02; B65D 50/067; B65D 50/068; B65D 55/02; B65D 55/022; B65D 55/024; B65D 55/04; B65D 55/10; B65D 55/14; B65D 51/18
USPC ........... 220/254.7, 288, 254.1, 266; 215/329, 215/330, 316, 200, 220, 253, 252, 277, 215/201, 250, 263, 204
See application file for complete search history.

(56) References Cited

U.S. PATENT DOCUMENTS

| | | | |
|---|---|---|---|
| 5,115,928 A * | 5/1992 | Drummond, Jr. | .... B65D 50/068 215/216 |
| 5,174,460 A | 12/1992 | Minnette | |
| 5,433,329 A | 7/1995 | Weinstein | |
| 6,082,564 A | 7/2000 | Trout | |
| 6,085,920 A | 7/2000 | Moretti | |
| 8,522,991 B2 | 9/2013 | Skelton et al. | |
| 2007/0090110 A1 | 4/2007 | Skelton et al. | |

FOREIGN PATENT DOCUMENTS

| | | |
|---|---|---|
| JP | S477907 Y1 | 3/1972 |
| JP | H03126150 U | 12/1991 |
| JP | H07013748 | 3/1995 |
| JP | H11180456 | 7/1999 |
| JP | 2002225906 | 8/2002 |
| JP | 2002225906 A | 8/2002 |
| JP | 2003104408 A | 4/2003 |
| WO | WO 2005/049443 | 6/2005 |

* cited by examiner

NON-REMOVABLE TAMPER RESISTANT LID

CROSS-REFERENCE TO RELATED APPLICATIONS

This application is a continuation of U.S. patent application Ser. No. 14/119,200, filed on Nov. 21, 2013, which is a national stage entry of PCT/EP2011/058960, filed on May 31, 2011, the disclosures of which are incorporated herein by reference in their entirety.

TECHNICAL FIELD

The present invention relates to a tamper resistant lid for sealing an opening of a container while at the same time, providing a tamper resistant lid which substantially prevents access to the container by preventing the lid from being removed from the container after it has been connected thereto.

BACKGROUND OF THE INVENTION

Hospitals, care centers, and the like, generally tend to use more and more disposable medical devices in their daily operation. Disposable medical devices are used as they generally require no post use sorting, sterilization or washing facilities. Instead, as their name suggests, they can simply be disposed. The amount of medical waste, such as used needles, contaminated medical devices, e.g. infusion sets or the like, is thus growing. Although there are several advantages with disposable items, medical waste generally tends to require considerations during and after disposal.

A nurse taking a blood sample using a needle, places the needle in a safe environment, i.e. an environment which has a limited access. The limited access after use prevents staff from unnecessary exposure and the risk there from. Sealable containers are frequently used for this purpose. Generally such sealable containers are made from stainless steel, aluminum or a similar metal, and after being filled with medical waste, the containers are simply sealed using an ordinary screw lid. The sealed containers can thereafter be brought to an incinerator for destruction or optionally for sterilization before going to a recycle plant or a land fill.

However, during use, e.g. as the sealed containers are moved to their end station, persons handling the sealed containers are exposed to the risk of accidentally opening the sealed container, or for any other reason, the sealed container would be opened or break. As such there is a constant need to improve the methods and devices used for sealing containers, and especially for sealing medical waste containers.

SUMMARY OF THE INVENTION

It is an object of the present invention to at least partly solve or reduce the effects of the drawbacks mentioned above. More specifically they are at least partly solved or reduced by a tamper resistant lid for a container according to the present invention. The lid exhibits a centre axis and comprises an outer and an inner member. The outer and inner members each comprise an outer and inner surface wherein at least a part of the outer surface of the inner member is substantially adjacent at least a part of the inner surface of the outer member. The outer and inner members are further substantially prevented from displacement along the centre axis with respect to each other. The inner member comprises connection means enabling a connection to the container by means of rotating the outer member in a first direction. The lid comprises at least one stop member preventing the inner member from rotation with respect to the outer member. The at least one stop member(s) is/are adapted to be controllably disabled with a designated force after the inner member has been connected to the container, so that the outer member can be freely rotated with respect to the inner member to thereby prevent the removal of the lid from the container.

The present invention provides for a tamper resistant lid which enables an improved handling in terms of safety and work environment. The tamper resistant lid effectively reduces the risk of accidentally opening sealed containers, while permitting a secure sealing of the container.

In an embodiment according to the present invention, the at least one stop member can be adapted to be disabled with a designated rupture force. The designated rupture force can be imparted to the at least one stop member by moving the outer member, with respect to the inner member, or by moving the at least one stop member itself in a designated direction or a first direction. Generally, the at least one stop member is moved with respect to the outer member. In this way, the at least one stop member can be disabled by rupturing the at least one stop member, and/or optionally the at least one stop member can be disabled by being removed.

In cases where the at least one stop member is arranged to fixedly connect the outer and the inner member of the lid, the at least one stop member can be ruptured by subjecting the at least one stop member to a designated rupture force, thereby enabling the outer member to be freely turned, i.e. rotated, with respect to the inner member. Alternatively, or additionally, at least one of the stop members can be adapted to be in working cooperation with the inner member. The at least one of the stop members can be in the form of a removable protrusion member, cooperative with a groove on the inner member for example.

According an embodiment to the present invention, at least one stop member is controllably disabled by a designated force in a designated direction. The designated direction can be in the same direction as the first direction. This is advantageous as a user simply continues the rotational motion, when screwing the lid onto e.g. a container, to disable the at least one stop member. Optionally, the designated direction can be in the direction of the centre axis (X). This can be advantageous in cases where a user want to make sure that a container is to be closed, but not disabling the at least one stop member. This can be done as the lid is threaded onto e.g. a container, while the at least one stop member is disabled by moving e.g. the outer member, with respect to the inner member in a direction substantially perpendicular to the first direction along which the lid is screwed onto a container. A user does thereby not risk disabling the at least one stop member(s) accidentally.

The at least one stop member can be arranged at many different locations depending on the desired designated direction for disabling the at least one stop member. Suitable locations are substantially between the inner and outer members or between the inner and outer members, as this is a simple yet effective way of preventing the outer member from motion with respect to the inner member, thereby enabling the lid to be screwed on a container, while afterwards disabling the at least one stop member. Optionally, the at least one stop member can be arranged between the inner surface of the outer member and the outer surface of the inner member.

In an embodiment according to the present invention, the at least one stop member can extend around the centre axis, e.g. as a ring or a polygonal, continuous or discontinuous around the centre axis. If there is a plurality of stop members, they can be positioned symmetrically around the centre axis for distributing the required designated rupture force required to disable the stop members. Optionally, if there is only one stop member, the stop member can in itself be arranged symmetrically around the centre axis, preferably between the inner and outer members. This will provide a good rupture surface between the outer and inner members after disabling the stop member. The inner and the outer members will not be inclined to reengage each other, thus not enabling the outer member to move the inner member. This advantage is also prominent if the at least one stop member is arranged to intersect the centre axis, i.e. is positioned between the inner and outer members and at the centre of the circular base of the inner and outer members.

The at least one stop member can be adapted to be controllably disabled by removal from the outer member. It/they will thus be prevented from interacting with the inner member to stop the inner member from being turned with respect to the outer member. According to one embodiment of the present invention, the at least one stop member can be removed by imparting a designated rupture force to the at least one stop member. In this embodiment, the at least one stop member is fixedly attached to the inner and/or the outer member before being removed by the imparted rupture force.

In an embodiment according to the present invention, the inner member, outer member and the at least one stop member can be integrally formed in one piece of material, e.g. by form molding or similar. Optionally, the outer and inner members are formed from separate pieces of material. The at least one stop member can be integrally formed by one piece of material with either the inner member and/or the outer member.

The present invention further relates to an assembly of a medical waste container and the tamper resistant lid as described herein. The assembly specifically relates to all the different embodiments described above and below, and as outlined in the claims. The present invention also relates to the use of a tamper resistant lid as described herein, or according to any of the claims, for sealing a medical waste container.

The present invention also relates to a method for sealing a container using a tamper resistant lid as described herein. The method comprises the steps of;
providing the lid;
screwing the lid onto the container;
disabling the at least one stop member.

The method enables the sealing of a container which sealing effectively prevents the container from being reopened.

The at least one stop member can be; one stop member, two stop members, three stop members, four stop members, or more. In some embodiments it can be advantageous to have 2-50 stop members, 5-40 stop members or optionally 10-30 stop members. According to an embodiment of the present invention, the stop member or the plurality of stop members can be formed by a pin, e.g. press fitted, which is arranged between the inner and outer member.

According to an aspect, an embodiment relates to a tamper resistant lid for a container. The lid comprises a centre axis X, an outer and an inner member. The outer and inner members are further substantially prevented from displacement along the centre axis X with respect to each other. At least a part of the inner member comprises threads enabling a threaded connection to the container by means of rotating the outer member in a first direction. The lid further comprises at least one stop member preventing the inner member from rotation with respect to the outer member. The at least one stop member is adapted to be controllably disabled with a designated force after the inner member has been connected to the container, so that the outer member can be freely rotated with respect to the inner member to thereby prevent removal of the lid from the container. The present invention enables the sealing of a container, while substantially preventing the container from being reopened.

Suitable materials for the inner and outer members are polymeric materials such as polyethylene, polypropylene, polyurethane, biopolymers, e.g. PPC, polyprophylene carbonate and/or starch, or the like, metals or alloys such as aluminum, alumina, brass, steel, iron or the like. Combinations of the above mentioned materials are of course also possible such as a metal outer member having an inner member made from a polymeric material, such as plastics, e.g. polypropylene. The outer member can advantageously be manufactured from a deformation resistant material such as steel or a thicker plastic material, to prevent or reduce the risk of that the outer member is deformed when subjected to a force. Such force could be imparted when the inner member is rotated by means of the outer member for example.

The inner member or outer member can be coated with a material to reduce the friction between the inner and the outer member. Optionally a friction reducing material can be positioned, chemically attached with e.g. adhesive or physically retained in position, between the inner and outer member.

Definitions

It should be noted that although it is said that removal of the tamper resistant lid is prevented after disabling the stop member, the term "prevented" is by no means to be interpreted as impossible to remove. A lid (or a container) can be broken whereafter the lid can be removed. Thus the term "prevented" is to be read as; prevented from removal using reasonable efforts or otherwise normal procedures.

BRIEF DESCRIPTION OF THE DRAWINGS

The present invention will be described in greater detail with reference to the accompanying figures in which.

DETAILED DESCRIPTION OF PREFERRED EMBODIMENTS

Figure 1:
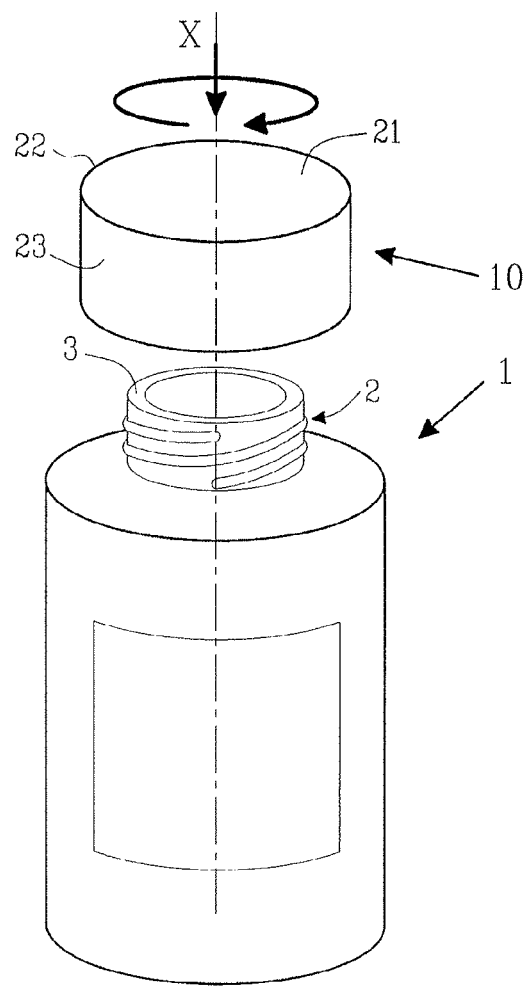
FIG. 1 shows a container and a tamper resistant lid according to one embodiment of the present invention.

FIG. 1 shows a medical waste container 1, hereafter referred to as the container, for storing hazardous waste such as used needles, contaminated medical equipment or the like. The tamper resistant lid 10 can however be used for any container to store hazardous material, goods, or the like. The container 1 can be sealed with a tamper resistant lid 10, also referred to as "the lid", according to one embodiment of the present invention. The lid 10 is suitably connected to the container 1 by means of a threaded coupling using threads 2 arranged on a neck element 3 of the container 1. The container 1 and the lid 10 are depicted with a centre axis X extending through the centre of the container 1 and the lid 10. When e.g. medical waste, in the form of used needles for example, has been placed in the container 1, the lid 10 can be threaded onto the neck element 3 to seal the interior of the container 1 from the ambient environment thus preventing access the container 1 and the medical waste. The lid 10 comprises at least one stop member which is adapted to enable the lid 10 to be screwed onto the neck element 3 and, after being connected thereto, disable the lid from being unscrewed from the neck element 3, to thereby prevent access to the interior of the container 1.

Figure 2:
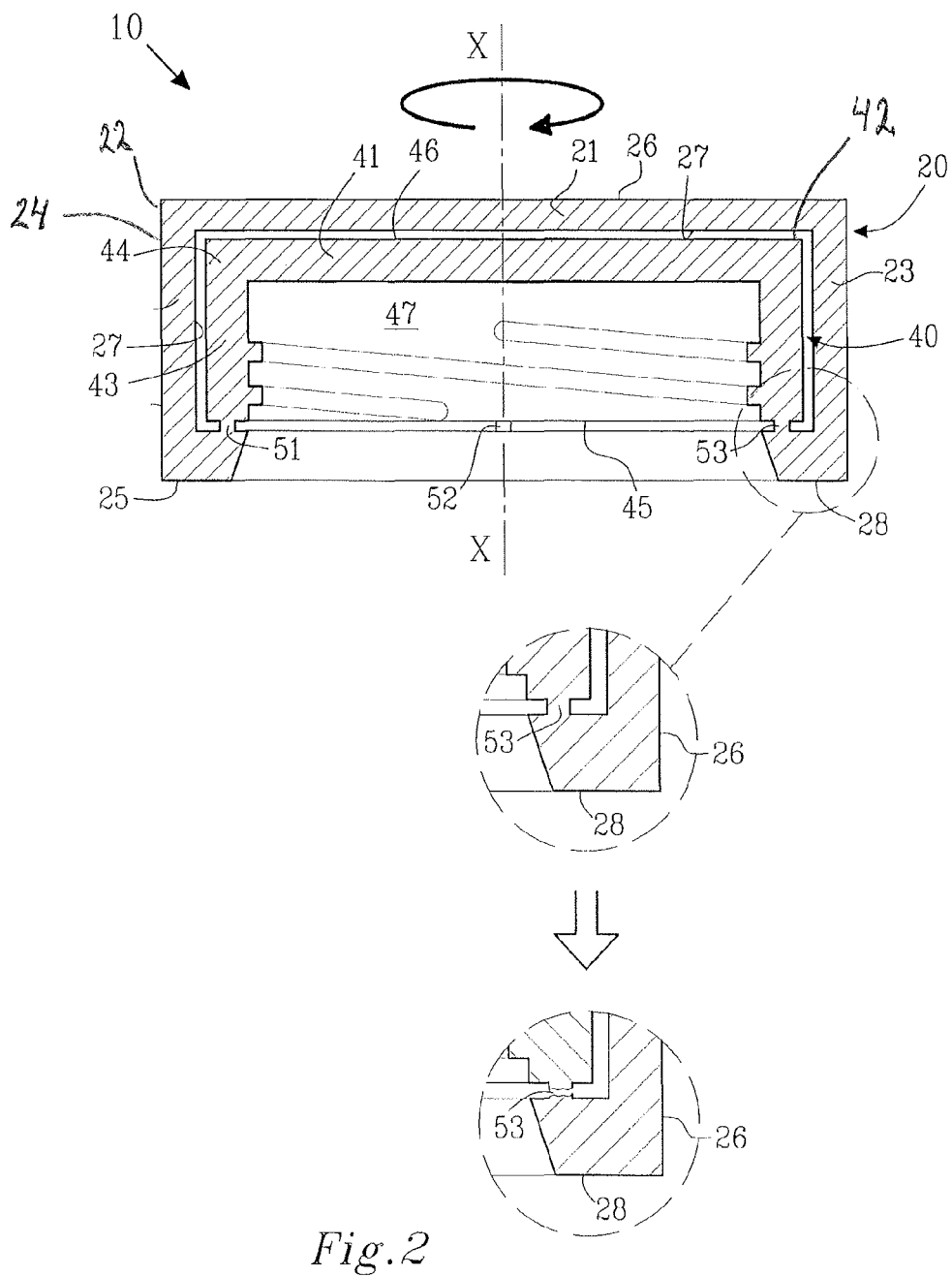
FIG. 2 shows a cross section of the tamper resistant lid shown in FIG. 1.

FIG. 2 shows a cross section of the tamper resistant lid 10 as shown in FIG. 1. The lid 10 comprises an outer member 20 substantially enclosing an inner member 40. The outer member 20 comprises a circular base 21 having a circular periphery 22. A circular wall 23 extends around the circular periphery 22, the circular wall has a proximal end 24 arranged on the circular base 21 and a distal end 25 arranged remotely from the circular base 21. The outer member 20 further exhibits an outer surface 26 and an inner surface 27. At least the inner surface 27 can have a smooth surface. At the distal end 25 of the circular wall 23, a circumferential lock flange 28, projects towards the centre axis X. The circumferential lock flange 28 is substantially preventing the inner member 40 from movement along the centre axis X in a direction away from the inner surface 27 of the outer member 20. It should be noted that although the circumferential lock flange 28 is said to prevent the inner member 40 from moving along the centre axis X with respect to the outer member 20, there can still be a play between the outer and inner members 20, 40 permitting a small relative displacement of the outer and inner members 20, 40.

The inner member 40 comprises a circular base 41 having a circular periphery 42. A circular wall 43 extends around the circular periphery 42. The circular wall 43 has a proximal end 44 arranged on the circular base 41 and a distal end 45 arranged remotely from the circular base 41. The inner member 40 further exhibits an outer surface 46 and an inner surface 47. The inner surface 47 exhibits connecting means, such as threads 48, for providing a threaded coupling with the threads 2 of the neck element 3 of the container 1. The distal end 45 of the circular wall 43 is in working cooperation with the circumferential lock flange 28 of the outer member 20, to prevent the inner member 40 from moving along the centre axis X and with respect to the outer member 20. As is noted, the inner surface 27 of the outer member 20 is substantially adjacent the outer surface 46 of the inner member 40, however a small play is possible.

A plurality of stop members 51, 52, 53 is arranged between the outer member 20 and the inner member 40, to prevent the inner member 40 from displacement, in this case from rotating, i.e. turning, with respect to the outer member 20. The shown embodiment in FIG. 2 shows only three stop members 51, 52, 53 although the lid 10 is equipped with four stop members. The plurality of stop members 51, 52, 53 are arranged symmetrically around the distal end 45 of the circular wall 43 and attaches the circumferential lock flange 28 of the outer member 20 thereto. As the lid 10 is screwed onto the neck element 3 of the container 1, the plurality of stop members 51, 52, 53 are adapted to rupture when being exposed to a designated rupture force, imparted by a user via the outer member 20. As the plurality of stop members 51, 52, 53 rupture, the fixed connection between outer and inner members is disabled, and the outer member 20 can be freely rotated with respect to the inner member 40. As the outer member 20 can be freely rotated with respect to the inner member 40, but is substantially prevented from displacement along the centre axis X, the outer member 20 substantially encloses the inner member 40 and prevents access to the inner member 40 for unscrewing the inner member 40 from the threads 2 of the neck element 3 of the container 1. As such, the tamper resistant lid 10 provides a lid which can be threaded onto an appropriate container, and subsequently prevented from being unscrewed from the container, to thereby expose the interior of the container to the ambient environment.

The play, mentioned above, between the outer and inner members 20, 40 permitting a relative displacement of the outer and inner member 20, 40, assists to disable the at least one stop member by permitting the outer member 20 to be imparted with a designated rupture force, e.g. in the direction of rotation or in a direction along the centre axis X. According to an aspect of the invention, the at least one stop member can be specifically configured to withstand a rotational motion while being configured to rupture as a function of a designated force imparted in a direction perpendicular to the rotational motion, and vice versa. According to an embodiment, a user can thus easily attach the lid to the container by a rotating motion and thereafter simply hit the lid with his/hers hand with a motion along the centre axis X to provide the designated rupture force to the plurality of stop members.

Figure 3A:
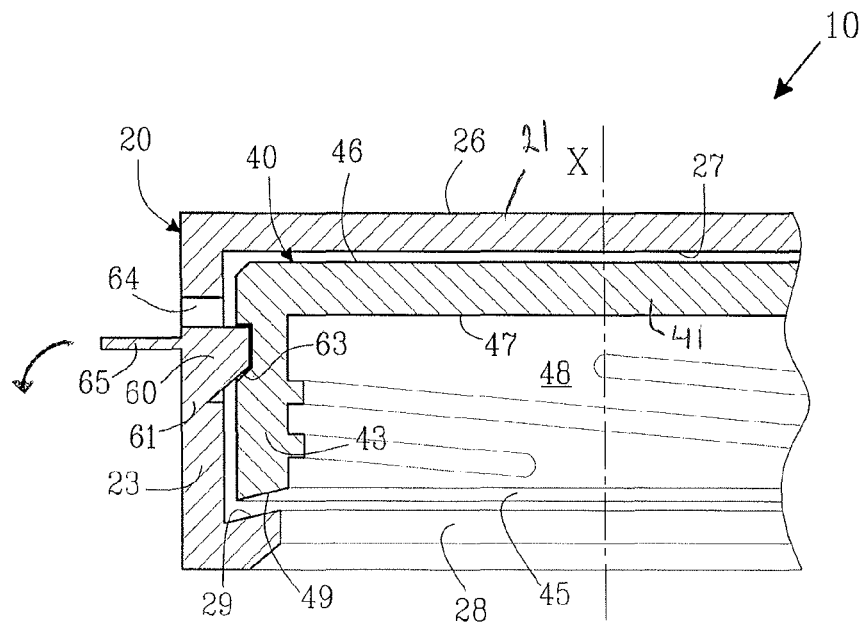
FIG. 3a-3b show a cross section of a tamper resistant lid according to a second embodiment of the present invention.
Figure 3B:
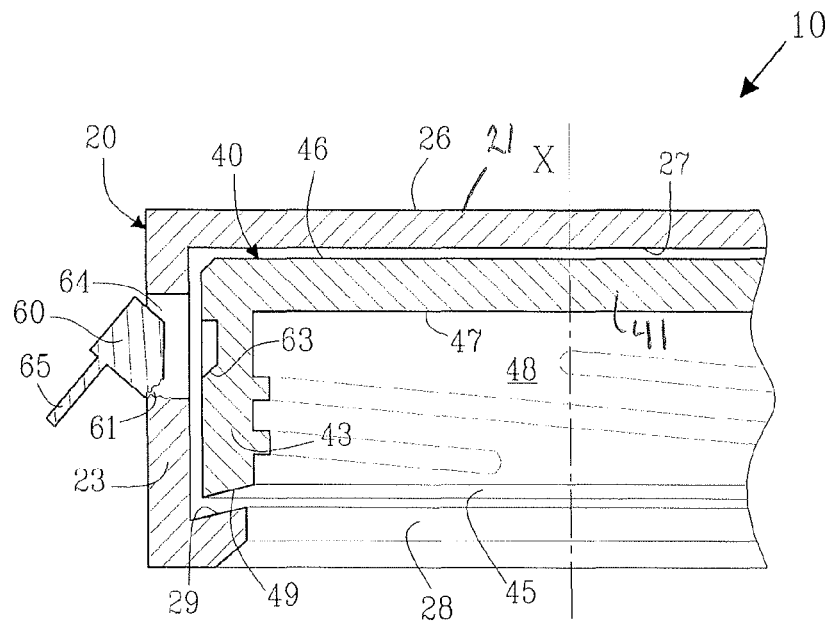

FIGS. 3a-3b show a cross section of a tamper resistant lid 10, according to a second embodiment of the present invention. For the sake of simplicity, only a part of the lid 10 is shown. The same references used above are used for the same features. The lid 10 comprises an outer and inner member 20, 40, each respectively comprising an outer and inner surface 26, 27, 46, 47, and a circular base 21, 41 having a circular wall 23, 43 extending around the periphery of the circular base 21, 41, as described above with reference to FIG. 2. The inner surface 47 of the inner member 40 is equipped with connecting means, such as threads 48.

The outer member 20 comprises at least one stop member 60, integrally formed with the outer member 20. The stop member(s) 60 is/are in working cooperation with a groove 63 formed in the outer surface 46 in the circular wall 43 of the inner member 40. The stop member 60, while being arranged partly inside the groove 63 of the inner member 40, as shown in FIG. 3a, effectively prevents the outer member 20 from being turned with respect to the inner member 40, thus permitting the lid 10 to be screwed onto the threads 2 of the neck element 3 of the container 1, as shown in FIG. 1. Optionally the at least one stop member can be integrally formed with the inner member 40 and in working cooperation with a groove or aperture formed in the inner surface 26 of the circular wall 23 of the outer member 20.

The stop member 60 is pivotally connected to the outer member 20 at a pivot point 61 and arranged in an opening 64, i.e. a through aperture, in the circular wall 23 of the outer member 20. The pivot point 61 permits the stop member 60 to be pivoted away from the groove 63 of the inner member 40, as indicated by the arrow in FIG. 3a, and optionally to be removed from the outer member 20 by fully rupture the connection between the stop member 60 and the outer member 20 at the pivot point 61. As the stop member 60 is removed from the groove 63, and removed from the outer member 20, the outer member 20 can be rotated, i.e. turned, clockwise or counter clockwise around the centre axis X, with respect to the inner member 40. As the outer member 20 substantially encloses the inner member 40, the inner member 40 is effectively prevented from being removed for the container 1, after assembly with the container 1. A grip member 65, extends away from the centre axis X, and is arranged on the stop member 60 enabling a user to readily grip and remove or displace the stop member 60. The shown embodiment can be provided with one or more stop members as just described. Furthermore, the one or more stop members can be interconnected so that they all can be removed with a single pull by a user.

As can be seen in FIGS. 3a and 3b, the opening 64 in the circular wall 23 of the outer member 20 further supports the stop member 60 when screwing the lid 10 onto e.g. the neck element 3 of the container 1. More specifically, the side walls of the opening 64 provide for the support as the stop member 60 is substantially prevented from motion in any direction along the turning direction, i.e. the clock wise or counter-clock wise rotational direction. The stop member 60 is thus snugly fitted in the opening 64 but is still permitted to be removed there from by disabling the stop member 60 in a predetermined, i.e. a designated direction, in this case, away from the outer member 20.

According to an embodiment of the present invention, the distal end 45 of the inner member 40 comprises a tilting surface 49 to enable a hook like lock configuration of the inner member 40 with respect to the outer member 20 together with a tilting surface 29, arranged on the circumferential lock flange 28 of the outer member 20. In a similar manner, the periphery 42 of the inner member 40 can be provided with a tilting surface to enable a smooth insertion of the inner member 40 into the outer member 20 during assembly of the outer and inner members 20, 40. As is noted, the stop member is also arranged with a tilting surface to simplify the assembly of the inner member 40 with the outer member 20 when manufacturing of the tamper resistant lid 10. As the inner member 40 is inserted into the inner member 20, the stop member 60 is pivoted, without rupturing, just enough to be displaced so that the inner member 40 can be inserted into the outer member 20. As the lid 10, and the outer member 20 is screwed onto e.g. the neck element 3 of the container 1, as shown in FIG. 1, the stop member 60 will automatically move, or pivot, into the groove 63 of the inner member 40. The stop member is thus advantageously biased in the direction of the centre axis X.

As is shown and described with reference to FIGS. 2, 3a-3b, the at least one stop member 51, 52, 53, 60 can be either fixed or movable. Common for the stop members 51, 52, 53, 60 is however that they all can be disabled. In the shown embodiments, they are disabled by means of imparting a rupture force to the at least one stop member(s) 51, 52, 53, 60. There are however other ways of disabling the at least one stop members, e.g. the at east one stop member(s) can be removed, if they are removably attached to the lid 10. Optionally the at least one stop member can be disabled by heat, if using e.g. a heat sensitive adhesive, or dissolved, if using a solvent sensitive adhesive, or by other means.

It should be noted that even though the claims are directed to a lid for a container, the lid could comprise optional components, such as a membrane.

What is claimed is:

1. A tamper resistant lid comprising:
a centre axis;
an outer member;
an inner member;
the outer member and the inner member each comprise an outer surface, an inner surface, a circular base having a circular wall extending around a periphery of the circular base wherein the outer surface in the circular wall of the inner member having a groove, the inner surface of the inner member having a thread enabling a connection to a container by means of rotating the outer member in a first direction; and
the outer member comprises at least one stop member, the at least one stop member being partly arranged inside the groove of the inner member preventing the inner member from rotation with respect to the outer member, the stop member is pivotally connected to the outer member at a pivot point and arranged in an opening in the circular wall of the outer member, wherein the at least one stop member is adapted to be removed from the outer member by full rupture of the connection between the stop member and the outer member at the pivot point after the inner member has been connected to the container, so that the outer member can be freely rotated with respect to the inner member to thereby prevent removal of the tamper resistant lid from the container.

2. The tamper resistant lid of claim 1, wherein the pivot point allows the stop member to be pivoted away from the groove of the inner member.

3. The tamper resistant lid of claim 1, wherein the at least one stop member is adapted to be disabled with a designated rupture force imparted to the at least one stop member by moving the outer member or the at least one stop member in a designated direction.

4. The tamper resistant lid of claim 3, wherein the designated direction is in the same direction as the first direction.

5. The tamper resistant lid of claim 3, wherein the designated direction is in the direction of the centre axis.

6. The tamper resistant lid of claim 1, further comprising a grip member.

7. The tamper resistant lid of claim 6, wherein the grip member extends away from the centre axis.

8. The tamper resistant lid of claim 6, wherein the grip member is arranged on the stop member.

9. The tamper resistant lid of claim 1, wherein the at least one stop member is arranged substantially between the inner member and the outer member.

10. The tamper resistant lid of claim 9, wherein the at least one stop member is arranged between the inner surface of the outer member and the outer surface of the inner member.

11. The tamper resistant lid of claim 10, wherein the at least one stop member is arranged symmetrically around the centre axis.

12. The tamper resistant lid of claim 1, wherein the at least one stop member is arranged on the outer member and adapted to be controllably disabled by removal from the outer member.

13. The tamper resistant lid of claim 12, wherein the at least one stop member is removed by imparting a designated rupture force to the at least one stop member.

14. The tamper resistant lid of claim 1, wherein the opening in the circular wall of the outer member supports the stop member.

15. An assembly comprising:
a medical waste container,
a tamper resistant lid comprising a centre axis;
an outer member;
an inner member;
the outer member and the inner member each comprise an outer surface, an inner surface, a circular base having a circular wall extending around a periphery of the circular base wherein the outer surface in the circular wall of the inner member having a groove, the inner surface of the inner member having a thread enabling a connection to a container by means of rotating the outer member in a first direction; and the outer member comprises at least one stop member, the at least one stop member being partly arranged inside the groove of the inner member preventing the inner member from rotation with respect to the outer member, the stop member is pivotally connected to the outer member at a pivot point and arranged in an opening in the circular wall of the outer member, wherein the at least one stop member is adapted to be removed from the outer member by full rupture of the connection between the stop member and the outer member at the pivot point after the inner member has been connected to the container, so that the outer member can be freely rotated with respect to the inner member to thereby prevent removal of the tamper resistant lid from the container.

16. The tamper resistant lid of claim 15, wherein the designated direction is in the direction of the centre axis.

* * * * *